US009636260B2

(12) United States Patent
Jenkins (10) Patent No.: US 9,636,260 B2
(45) Date of Patent: May 2, 2017

(54) CUSTOM MICROPHONES CIRCUIT, OR LISTENING CIRCUIT

(71) Applicant: Honeywell International Inc., Morristown, NJ (US)

(72) Inventor: John Jenkins, San Diego, CA (US)

(73) Assignee: Honeywell International Inc., Morris Plains, NJ (US)

(*) Notice: Subject to any disclaimer, the term of this patent is extended or adjusted under 35 U.S.C. 154(b) by 112 days.

(21) Appl. No.: 14/590,706

(22) Filed: Jan. 6, 2015

(65) Prior Publication Data

US 2016/0193084 A1    Jul. 7, 2016

(51) Int. Cl.
| | |
|---|---|
| *A61F 11/06* | (2006.01) |
| *A61F 11/14* | (2006.01) |
| *G10K 11/178* | (2006.01) |
| *H04R 1/10* | (2006.01) |

(52) U.S. Cl.
CPC ............ *A61F 11/14* (2013.01); *G10K 11/178* (2013.01); *A61F 2011/145* (2013.01); *G10K 2210/1081* (2013.01); *G10K 2210/3014* (2013.01); *G10K 2210/3039* (2013.01)

(58) Field of Classification Search
CPC .. A61F 11/14; A61F 2011/145; G10K 11/002; G10K 11/178; G10K 2210/1081; G10K 2210/3014; G10K 2210/3039
USPC ...................................................... 381/72, 74
See application file for complete search history.

(56) References Cited

U.S. PATENT DOCUMENTS

| | | | |
|---|---|---|---|
| 6,041,126 A | 3/2000 | Terai et al. | |
| 2002/0080979 A1* | 6/2002 | Brimhall | A61F 11/08 381/72 |
| 2003/0228023 A1 | 12/2003 | Burnett et al. | |
| 2008/0112570 A1 | 5/2008 | Asada et al. | |
| 2008/0267416 A1* | 10/2008 | Goldstein | H04R 1/1091 381/56 |
| 2008/0310645 A1 | 12/2008 | Itabashi et al. | |
| 2011/0096939 A1 | 4/2011 | Ichimura | |
| 2011/0116646 A1 | 5/2011 | Sander et al. | |
| 2011/0130176 A1 | 6/2011 | Magrath et al. | |
| 2011/0206217 A1 | 8/2011 | Weis | |
| 2012/0310636 A1 | 12/2012 | Ookuri et al. | |
| 2013/0287218 A1 | 10/2013 | Alderson et al. | |

(Continued)

FOREIGN PATENT DOCUMENTS

| | | |
|---|---|---|
| JP | 2014030254 A | 2/2014 |
| MX | 9709817 A | 3/1998 |

(Continued)

*Primary Examiner* — Xu Mei
*Assistant Examiner* — Ammar Hamid
(74) *Attorney, Agent, or Firm* — Conley Rose, P.C.; Kristin Jordan Harkins (57) ABSTRACT

Embodiments of the disclosure include hearing protection earmuffs, which generally might have two earcups providing passive noise reduction (e.g. an effective NRR to protect a user from a damaging external noise environment). Disclosed embodiments include systems and methods for transmitting external sounds to a speaker within the earcup, blocking transmission of sounds that are higher than a hearing protection threshold, amplifying sounds that are below the hearing protection threshold, and reducing or filtering undesirable background sounds by determining the frequency of the transmitted sounds.

20 Claims, 3 Drawing Sheets

(56) References Cited

U.S. PATENT DOCUMENTS

| | | |
|---|---|---|
| 2014/0126733 A1 | 5/2014 | Gauger, Jr. et al. |
| 2014/0126734 A1 | 5/2014 | Gauger, Jr. et al. |
| 2014/0126736 A1 | 5/2014 | Gauger, Jr. et al. |
| 2015/0117660 A1* | 4/2015 | Fletcher ............... G10K 11/178 381/72 |

FOREIGN PATENT DOCUMENTS

| | | |
|---|---|---|
| WO | 2009134107 A2 | 11/2009 |
| WO | 2010007825 A1 | 1/2010 |

* cited by examiner

CUSTOM MICROPHONES CIRCUIT, OR LISTENING CIRCUIT

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Some safety equipment hearing protection devices, such as passive noise reduction earcups (or earmuffs), also have speakers included therein (for example, for communication and/or entertainment functions). However, it makes no sense to protect a user from external noise which might cause hearing damage or loss, while simultaneously allowing the speakers to broadcast at such a high sound level that they may cause damage to the user's hearing. Thus, there may be a need to limit speaker output to safe levels. Additionally, sounds transmitted to the speakers may be amplified when they are lower than a desired decibel level.

SUMMARY

Aspects of the disclosure may include embodiments of a method for transmitting external sound through a hearing protection earcup comprising: detecting external sounds outside the earcup; analyzing the detected sounds to determine decibel level and frequency of the sound; determining to transmit the detected sounds when the decibel level is lower than a preset hearing protection threshold; and determining to filter the detected sounds when the frequency is within a preset range for an undesired background sound.

In some embodiments, the method may further comprise determining to block the detected sounds when the decibel level is higher than the preset hearing protection threshold. In some embodiments, the method may further comprise determining to reduce the detected sounds down to the hearing protection threshold when the decibel level is higher than the preset hearing protection threshold. In some embodiments, the method may further comprise determining to amplify the detected sounds up to the hearing protection threshold when the decibel level is lower than the preset hearing protection threshold. In some embodiments, the method may further comprise transmitting the detected sounds that are determined to be transmitted to an internal speaker inside the earcup. In some embodiments, the undesired background sound may comprise HVAC sounds. In some embodiments, the preset hearing protection threshold may be approximately 82 decibels. In some embodiments, analyzing the detected sounds to determine the decibel level and the frequency of the sound may further comprise receiving frequency signals from a microphone, wherein the microphone comprises sensitivity for the present frequency range.

Additional aspects of the disclosure may include embodiments of a hearing protection device comprising: a passive protection earcup comprising a hollow shell operable to encompass the ear of a user and having an air space volume to provide sufficient noise reduction rating (NRR); one or more external microphones operable to pick up external sounds; one or more internal speaker located within the earcup operable to direct sound into a user's ear; and circuitry operable to: determine the decibel level and frequency of sounds received from the microphone; allow pass-through of sounds to the speaker when the decibel level is lower than a hearing protection threshold; amplify sounds to the speaker up to a preset desired decibel level; and filter out undesired background sounds at a preset frequency.

In some embodiments, the circuitry may be further operable to block pass-through of sounds from the microphone to the speaker when the decibel level is higher than the hearing protection threshold. In some embodiments, the circuitry may be further operable to reduce the decibel level of sounds to the present desired decibel level. In some embodiments, the preset desired level may be equal to the hearing protection threshold. In some embodiments, the preset desired level may be customizable by a user. In some embodiments, the undesired background sounds may comprise HVAC sounds. In some embodiments, the undesired background sounds may comprise a frequency between approximately 0 and 5000 Hertz. In some embodiments, the speakers may be operable to transmit external sounds only.

Other aspects of the disclosure may include embodiments of a hearing protection headset comprising: two passive protection earcups comprising a hollow shell operable to encompass the ear of a user; a headband connecting the two earcups operable to provide sufficient clamping force to maintain an airtight seal between the exterior and interior of the earcups; one or more external microphones operable to pick up external sounds; one or more internal speaker located within the earcups operable to direct sound into a user's ear, wherein the speakers are operable to transmit external sounds only; and circuitry operable to: determine the decibel level and frequency of sounds received from the microphone; allow pass-through of sounds to the speaker when the decibel level is lower than a hearing protection threshold; amplify sounds to the speaker up to a preset desired decibel level; and filter out undesired background sounds at a preset frequency range.

In some embodiments, the microphone(s) may comprise sensitivity for the preset frequency range. In some embodiments, the circuitry may be further operable to block pass-through of sounds from the microphone to the speaker when the decibel level is higher than the hearing protection threshold. In some embodiments, the circuitry may be further operable to reduce the decibel level of sounds to the present desired decibel level.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Disclosed embodiments typically relate to heating protection earcups (or earmuffs), which generally might have two earcups providing passive noise reduction (e.g. an effective NRR to protect a user from a damaging external noise environment). More specifically, disclosed embodiments relate to such hearing protection earcups having a speaker therein (for example, for use in conjunction with communications gear, to receive input from an external microphone, and/or entertainment equipment (such as a music player)). This is safety equipment, however, so it may be important to ensure that the earcup's NRR is not unduly affected by the speaker (e.g. the NRR rating of the earcup typically should still be sufficiently high to protect the user), and to ensure that the speaker itself does not cause any hearing damage to the user. Additionally, some sounds transmitted to the speaker may be at lower decibels levels, so it may be desired to amplify sounds up to a preset desired decibel level. However, when sounds are amplified and sent to the speaker, undesired background sounds may also be picked up and amplified, causing desired sounds, such as talking, to be diluted or covered. Undesirable background sounds may include MAC system noise, traffic noise, machinery noise, aircraft noise, etc. Disclosed embodiments include systems and methods for transmitting external sounds to a speaker within the earcup, blocking transmission of sounds that are higher than a hearing protection threshold, amplifying sounds that are below the hearing protection threshold, and reducing or filtering undesirable background sounds by determining the frequency of the transmitted sounds.

Figure 1:
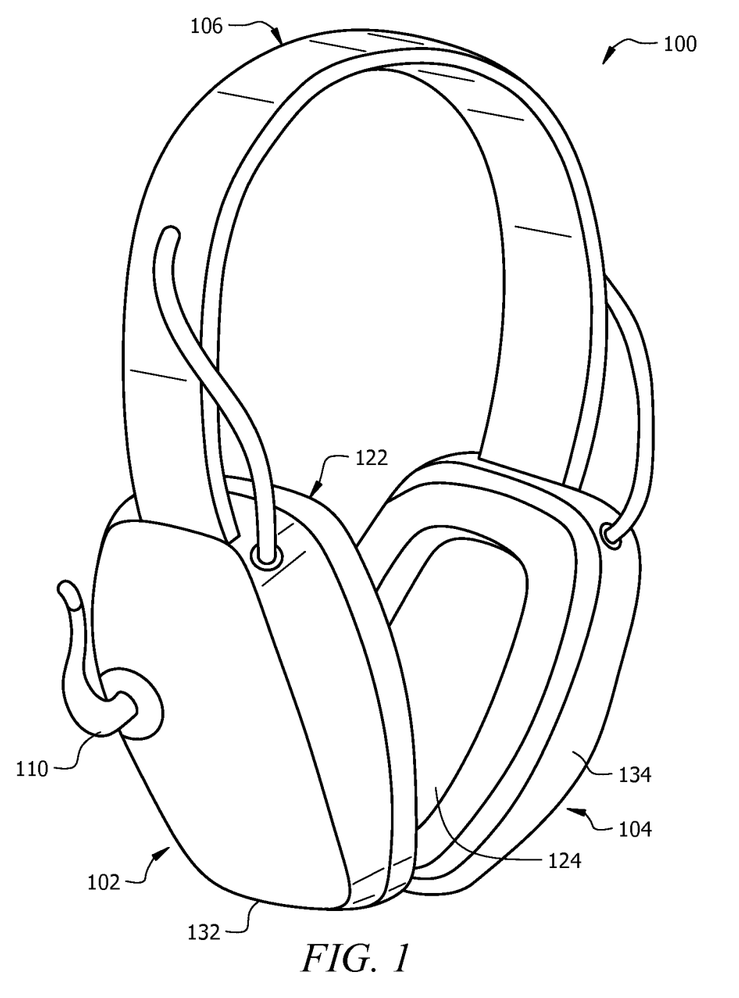
FIG. 1 illustrates an exemplary embodiment of a hearing protection headset.

Referring now to FIG. 1, an exemplary embodiment of a hearing protection headset 100 is shown. The headset 100 comprises a headband 106 connected to two earcups 102 and 104. The earcup 102 comprises an inner surface 122 and a exterior surface 132, and the earcup 104 comprises an inner surface 124 and an exterior surface 134, wherein the inner surfaces 122 and 124 contact and/or encompass the ears of a user. In some embodiments, the headset 100 may comprise at least one microphone 110 on the exterior surface 132 of one of the earcups 102, wherein the microphone 110 is operable to pick up sounds external to the earcups.

Figure 2:
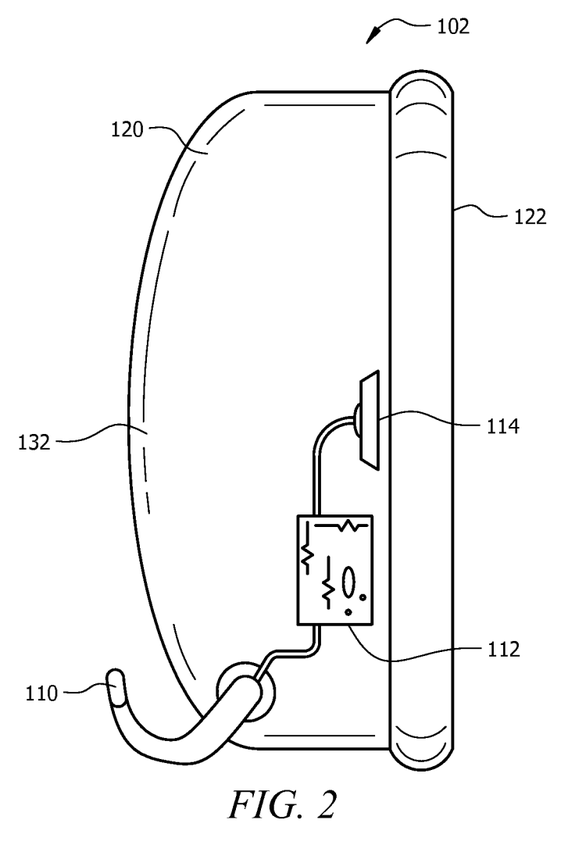
FIG. 2 illustrates schematically a cross-section of an exemplary embodiment of an earcup.

Referring now to FIG. 2, a detailed cross-sectional view of an earcup 102 is shown. The earcup 102 comprises a microphone 110 on the exterior 132 of the earcup 102 and a speaker 114 on the interior 122 of the earcup 102. The microphone 110 and speaker 114 may be connected by circuitry 112, wherein the circuitry 112 may comprise wires, receivers, transmitters, transceivers, amplifiers, filters, reducers, and other elements, as understood by persons of skill in the art field. In some embodiments, the speaker 114 may be operable to only transmit external sounds received from the microphone 110 via the circuitry 112. In some embodiments, the earcup 104 (not shown) may comprise similar elements as described in for the earcup 102.

To provide passive hearing protection, the earcup 102 may further comprise an airspace 120 (e.g. open volume of air, for ex. 100,000-300,000 cubic millimeters volume) and/or sound absorbing foam (e.g. reticulated and/or non-reticulated foam with thickness ranging from 1 mm up to the entire open volume of the cup). In some embodiments, the earcup 102 may also comprise a sealing section (on the interior surface 122), operable to seal the user's ear canal (for better passive noise reduction). Typically, the earcup may provide at least passive NRR of 20 or 25 by sealing a user's ear canal with the earcup.

Since embodiments relate to passive noise reduction earcups 102 for hearing protection, design of the earcups to provide effective passive NRR may often be quite important (and indeed may often be the driving factor for the design). Selecting/designing an earcup may comprise maximizing interior airspace while maintaining an acceptable low (exterior) profile, managing the weight of the hearing protection device/earcup so that it remains comfortable to the user, and/or selecting a clamping force (for example, for the headband linking the two earcups) sufficient to maintain an airtight seal between the exterior environment airspace and the interior airspace of the earcups while also remaining sufficiently comfortable for a user to wear over long periods. So for example, the earcup 102 might typically have 100,000 to 300,000 cubic millimeters air space volume 120 (for example, about 220,000 cubic millimeters in some embodiments) behind the speaker 114 (to help ensure effective passive NRR). Regardless, the earcup 102 typically is designed to provide adequate/effective hearing protection from external noise environments (for example noise environments in a range of 90-110 dB, such as airports, construction sites, or industrial plants). In some embodiments, the passive hearing protection provided by the earcup 102 may also comprise the use of foam within the cavity 120 of the earcups 102.

Typically, the speaker 114 would be located at or near the inner surface 122 of the opening of the earcup 102. (for example, just inside the earcup and facing the user's ear canal, below the most exterior part of the cushion), and the circuitry may be located close to the exterior wall 132 of the earcup shell (e.g. so the method might comprise placing the speaker and amplifier in the earcup in the desired location). Additionally, method embodiments might include electrically connecting the circuitry to the speaker (e.g. so that the speaker would be driven by the circuitry).

Such method embodiments (of the sort described above for example) typically would result in device embodiments which may provide improved features. For example, a hearing protection device embodiment might comprise: an earcup (for example, providing at least NRR of 20 or NRR in a range of 20-30 (or 25-30) and/or at least 100,000 cubic millimeters (or 100,000-300,000 cubic millimeters) of air space volume behind the speaker, etc.); a speaker (located within the earcup); and circuitry (located within the earcup and in electrical connection with the speaker (e.g. wherein the circuitry drives the speaker)); wherein the speaker provide a maximum speaker output which is limited (e.g. capped) typically precisely/exactly to a desired cap level (for example, the maximum legally allowed continuous noise exposure level, for example for an 8 hour period). For example, in the United States the maximum legally allowed continuous noise exposure level might be the limit set by OSHA or NIOSH (e.g. National Institute of Occupational Safety and Health). So under current U.S. government regulations, the speaker output might be limited to a level of about 82-95 dB, 82-85 dB, or 85-90 dB (for example, preferably 82 dB or 85 dB).

Figure 3A:
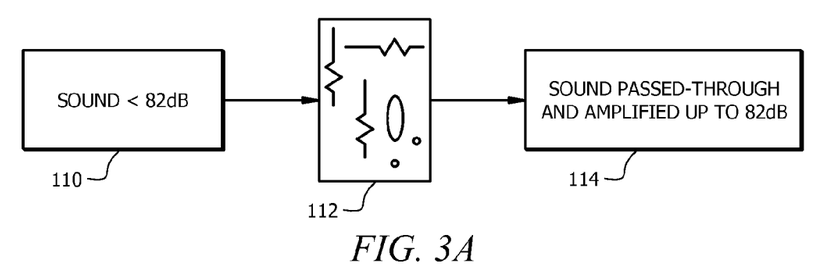
FIGS. 3A-3C illustrate schematically the interaction of elements for an improved method of transmitting external sounds through a hearing protection earcup via circuitry and a speaker.
Figure 3B:
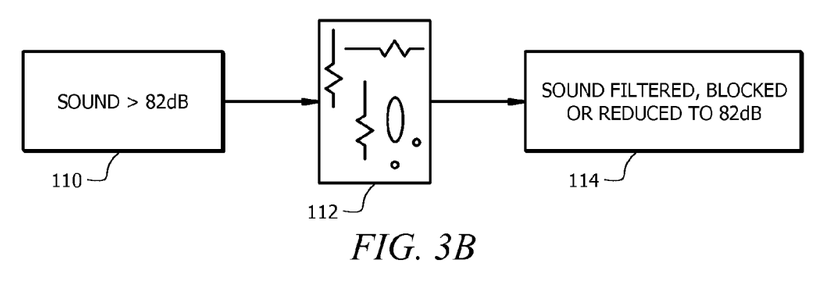
Figure 3C:
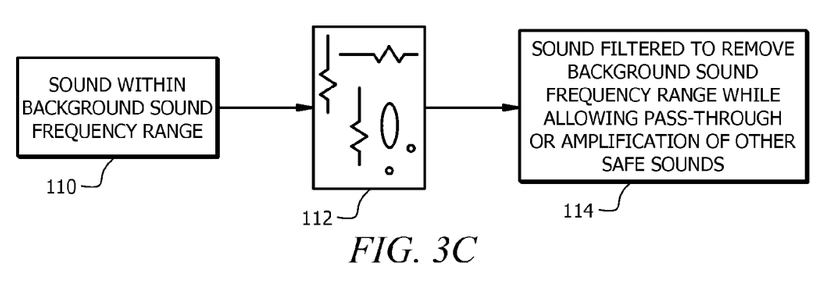

Referring now to FIGS. 3A-3C, the interaction between the microphone, circuitry, and speaker is described. In the embodiments described, the circuitry may control the transmission of external sounds that are detected by the microphone to the speaker by allowing transmission, amplifying the transmission, reducing the transmission, filtering the transmission, and/or blocking the transmission. The circuitry may be operable to analyze the sounds transmitted from the microphone, process the sound transmission, by determining manipulations of the transmission for example, and then send the sound transmission to the speaker.

For example, in FIG. 3A, the microphone 110 may transmit sounds that are lower than a hearing protection threshold. The threshold may be approximately 82 dB (or another threshold as described above). The circuitry 112 may analyze the transmission from the microphone 110 to determine dB level and frequency. When the circuitry 112 determines that the transmitted sounds are lower than the hearing protection threshold, the circuitry 112 may determine to amplify the transmission up to approximately 82 dB to be passed through to the speaker. In other embodiments, the circuitry 112 may determine to amplify the transmission up to a preset desired decibel level that may be lower than the hearing protection threshold. In some embodiments, the preset desired decibel level may be customizable by a user. In other embodiments, the sound may be passed through to the speaker and not amplified by the circuitry.

In another example, in FIG. 3B, the microphone 100 may transmit sounds that are higher than the hearing protection threshold. The circuitry 112 may analyze the transmission from the microphone 110 to determine the dB level and/or frequency. When the circuitry 112 determines that the transmitted sounds are higher than the hearing protection threshold, the circuitry 112 may determine to filter or block the transmitted sounds, so that none of the sounds are passed through to the speaker. In another embodiment, the circuitry may determine to reduce the transmitted sounds down to approximately 82 dB, or down to a preset desired decibel level.

In yet another example, in FIG. 3C, the microphone 110 may transmit sounds that include undesirable background sounds, such as HVAC system noise, traffic noise, machinery noise, aircraft noise, etc. The frequency range for exemplary background sounds may be between approximately 0 and 5000 Hertz. The circuitry 112 may analyze the transmission from the microphone 110 to determine the dB level and/or frequency. When the circuitry 112 determines that the transmitted sounds are within a preset frequency range (for undesirable background sound), the circuitry 112 may determine to filter the transmission to remove the background sound frequency range(s) while allowing pass-through or amplification of other safe sounds (that are lower than the hearing protection threshold). In some embodiments, the microphone may comprise sensitivity for the present undesired frequency range.

In headphone or earmuff embodiments having two earcups (one for each ear of the user), some of the elements described above might be associated with only one earcup (for example, the two earcups might share some elements, as discussed above with respect to FIG. 1, for example). Additionally, some embodiments might not actually include an earcup (but otherwise be similar to the various embodiments described above), for example being earbuds or headphones that do not seal the user's ear canal but which fit over or within the ear canal opening so that the speaker array may provide active noise cancellation to the user's ears.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior an to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method for transmitting external sound through a hearing protection earcup comprising:
    detecting, via a microphone and circuitry of a hearing protection earcup, external sounds outside the earcup;
    analyzing, by the circuitry of the hearing protection earcup, the detected sounds to determine decibel level and frequency of the sound;
    determining, by the circuitry of the hearing protection earcup, to transmit the detected sounds when the decibel level is lower than a preset hearing protection threshold; and
    determining, by the circuitry of the hearing protection earcup, to filter the detected sounds when the frequencies of the detected sounds are constant and within a preset frequency range for an undesired background sound;
    continuing, to transmit, by the circuitry, detected sounds only for the frequencies of the detected sounds outside of the preset frequency range for undesired backoround sound and only when the decibel level is lower than the preset hearing protection threshold.

2. The method of claim 1, further comprising determining, by the circuitry of the hearing protection earcup, to block the detected sounds when the decibel level is higher than the preset hearing protection threshold.

3. The method of claim 1, further comprising determining, by the circuitry of the hearing protection earcup, to reduce the detected sounds down to the hearing protection threshold when the decibel level is higher than the preset hearing protection threshold.

4. The method of claim 1, further comprising determining, by the circuitry of the hearing protection earcup, to amplify the detected sounds up to the hearing protection threshold when the decibel level is lower than the preset hearing protection threshold.

5. The method of claim 1, wherein the earcup comprises at least one speaker internal to the earcup that is configured to transmit the detected sounds that are determined to be transmitted.

6. The method of claim 1, wherein the undesired background sound comprises heating, ventilating, and air conditioning (HVAC) sounds.

7. The method of claim 1, wherein the preset hearing protection threshold is approximately 82 decibels and wherein the preset frequency range is between approximately 50 and 5000 Hertz.

8. The method of claim 1, wherein analyzing the detected sounds to determine the decibel level and the frequency of the sound further comprises receiving frequency signals from a microphone, wherein the microphone comprises sensitivity for the preset frequency range.

9. A hearing protection device comprising:
    a passive protection earcup comprising a hollow shell operable to encompass the ear of a user and having an air space volume to provide sufficient noise reduction rating (NRR);
    one or more external microphones operable to pick up external sounds;
    one or more internal speakers located within the earcup operable to direct sound into a user's ear; and
    circuitry operable to:
        determine the decibel level and frequency of sounds received from the microphone;
        allow pass-through of sounds to the speaker when the decibel level is lower than a hearing protection threshold;
        amplify sounds to the speaker up to a preset desired decibel level that is not above the hearing protection threshold; and
        filter out undesired background sounds when the sounds are comprised of frequencies that are approximately constant and within a preset frequency range.

10. The device of claim 9, wherein the circuitry is further operable to block pass-through of sounds from the microphone to the speaker when the decibel level is higher than the hearing protection threshold.

11. The device of claim 9, wherein the circuitry is further operable to reduce the decibel level of sounds to the preset desired decibel level.

12. The device of claim 9, wherein the preset desired level is equal to the hearing protection threshold.

13. The device of claim 9, wherein the preset desired level is customizable by a user.

14. The device of claim 9, wherein the undesired background sounds comprise heating, ventilating, and air conditioning (HVAC) sounds.

15. The device of claim 9, wherein the undesired background sounds comprise a frequency between approximately 50 and 5000 Hertz.

16. The device of claim 9, wherein the speakers are operable to transmit external sounds only.

17. A hearing protection headset comprising:
  two passive protection earcups comprising a hollow shell operable to encompass the ear of a user;
  a headband connecting the two earcups operable to provide sufficient clamping force to maintain an airtight seal between the exterior and interior of the earcups;
  one or more external microphones operable to pick up external sounds;
  one or more internal speakers located within the earcups operable to direct sound into a user's ear, wherein the speakers are operable to transmit external sounds only; and
  circuitry operable to:
    determine the decibel level and frequency of sounds received from the microphone;
    allow pass-through of sounds to the speaker when the decibel level is lower than a hearing protection threshold;
    amplify sounds to the speaker up to a preset desired decibel level that is not above the hearing protection threshold;
    filter out undesired background sounds when the sounds are comprised of frequencies that are constant and within a preset frequency range; and
    allow pass-through and amplification of sounds that have frequencies outside of the preset frequency range and decibel levels below the hearing protection threshold.

18. The headset of claim 17, wherein the microphone(s) comprise sensitivity for the preset frequency range.

19. The headset of claim 17, wherein the circuitry is further operable to block pass-through of sounds from the microphone to the speaker when the decibel level is higher than the hearing protection threshold.

20. The device of claim 17, wherein the circuitry is further operable to reduce the decibel level of sounds to the preset desired decibel level.

* * * * *

UNITED STATES PATENT AND TRADEMARK OFFICE
CERTIFICATE OF CORRECTION

PATENT NO.        : 9,636,260 B2
APPLICATION NO.   : 14/590706
DATED             : May 2, 2017
INVENTOR(S)       : John Jenkins It is certified that error appears in the above-identified patent and that said Letters Patent is hereby corrected as shown below:

Column 7, Line 61: "continuing," should be "continuing"

Column 7, Line 63: "backoround" should be "background"

Signed and Sealed this
Twenty-fourth Day of October, 2017

Joseph Matal
*Performing the Functions and Duties of the
Under Secretary of Commerce for Intellectual Property and
Director of the United States Patent and Trademark Office*